United States Patent
Ozaki et al.

(10) Patent No.: US 7,423,032 B2
(45) Date of Patent: Sep. 9, 2008

(54) METHOD FOR TREATING SEVERE HEART FAILURE AND MEDICAMENT THEREFOR

(75) Inventors: Atsushi Ozaki, Gaithersburg, MD (US); Yosuke Maki, North Potomac, MD (US); Osamu Sato, Toyonaka (JP); Yoshitaka Yamamura, Gaithersburg, MD (US)

(73) Assignee: Otsuka Pharmaceutical Co., Ltd., Tokyo-to (JP)

( * ) Notice: Subject to any disclaimer, the term of this patent is extended or adjusted under 35 U.S.C. 154(b) by 216 days.

(21) Appl. No.: 10/523,020

(22) PCT Filed: Feb. 23, 2004

(86) PCT No.: PCT/JP2004/002085

§ 371 (c)(1),
(2), (4) Date: Feb. 2, 2005

(87) PCT Pub. No.: WO2004/073716

PCT Pub. Date: Sep. 2, 2004

(65) Prior Publication Data

US 2005/0187210 A1 Aug. 25, 2005

Related U.S. Application Data

(60) Provisional application No. 60/448,878, filed on Feb. 24, 2003.

(51) Int. Cl.
*A61K 31/55* (2006.01)
(52) U.S. Cl. .................................. 514/213.01
(58) Field of Classification Search ............ None
See application file for complete search history.

(56) References Cited

U.S. PATENT DOCUMENTS

| 5,258,510 | A | 11/1993 | Ogawa |
| 5,753,677 | A | 5/1998 | Ogawa |
| 5,827,862 | A | 10/1998 | Yamamura |
| 2002/0128259 | A1 | 9/2002 | Ghazzi et al. |
| 2003/0008860 | A1 | 1/2003 | Bakker-Arkema et al. |
| 2004/0176354 | A1 | 9/2004 | Arkema et al. |

FOREIGN PATENT DOCUMENTS

| JP | A-06-80641 | 3/1994 |
| JP | A-80641 | 3/1994 |
| JP | A-7-188021 | 7/1995 |
| JP | A-8-157368 | 6/1996 |
| JP | A-10-120592 | 5/1998 |
| JP | 11 021241 A | 1/1999 |
| WO | WO 94/01113 | 1/1994 |
| WO | WO 01/54677 | 8/2001 |

OTHER PUBLICATIONS

L. A. Sorbera et al., "Tolvaptan," Drugs of the Future, 2002, vol. 27, No. 4, pp. 350-357.
Alberto Martinez-Castelao, OPC-31260 Otsuka, "Current Opinion in Cardiovascular, Pulmonary & Renal Investigational Drugs," 1999, vol. 1, No. 3, pp. 423-432.
Toshio Nishikimi et al., "Effect of Long-Term Treatment with Selective Vasopressin V1 and V2 Receptor Antagonist on the Development of Heart Failure in Rats," Journal of Vardiovascular Pharmacology, 1996; vol. 27, No. 2 pp. 275-282.
Keishi Shimizu et al., Effects of Oral OPC-31260, a Vasopressin $V_2$-Receptor Antagonist Administration on Arterial Baroreceptor Reflex in Conscious Intact and Adriamycin-Induced Heart Failure Rats, Naika Hokan, 1993, vol. 40, No. 1, pp. 7-11.
Louise M. Burrell et al., Long-Term effects of nonpeptide vasopressin V2 antagonist OPC-31260 in heart failure in the rat, American Journal of Physiology, 1998, vol. 275, No. 1, pp. H-176-H182.
Mareo Naitoh et al., Effects of oral AVP receptor antagonists OPC-21268 and OPC-31260 on congestive heart failure In conscious dogs, American Journal of Physiology, 1994, vol. 267, No. 6, Part 2, pp. H2245-H2254.
Taresh Taneja et al., "Current Status of Acute Intravenous Therapy for Chronic Heart Failure Exacerbations," CHF Sep./Oct. 1999, pp. 199-207, 215.
Leonard Arnolda et al., "Vasopressin and angiotensin II contribute equally to the increased afterload in rabbits with heart failure," Cardiovascular Research 1991; 25: pp. 68-72.

(Continued)

*Primary Examiner*—Raymond J Henley, III
(74) *Attorney, Agent, or Firm*—Finnegan, Henderson, Farabow, Garrett & Dunner, L.L.P.

(57) ABSTRACT

A method for treating severe heart failure, comprising administering to a patient an effective amount of a benzazepine compound (1): wherein $R_1$ is H or halogen, $R_2$ is OH, or —$NR_5R_6$ ($R_5$ and $R_6$ are H or lower alkyl, $R_3$ is H, halogen, lower alkyl, or lower alkoxy, $R_4$ is halogen, lower alkyl or lower alkoxy, or a salt thereof, and a pharmaceutical composition containing the benzazepine compound (1) or a salt thereof and use of the compound (1) or a salt thereof for preparing a medicament for treatment of severe heart failure

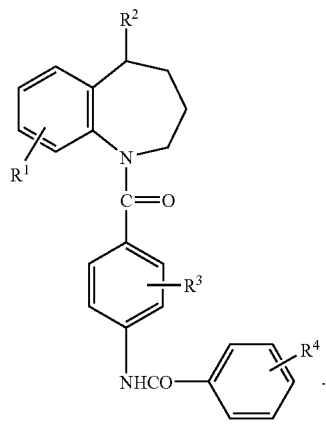

4 Claims, No Drawings

OTHER PUBLICATIONS

Mihai Gheorghiade et al., "Rationale and study design for a multicenter, randomized, double-blind, placebo-controlled study of the effects of tolvaptan on the acute and chronic outcomes of patients hospitalized with worsening congestive heart failure," American Heart Journal, vol. 145, No. 2, Feb. 2003; pp. S51-4.

C, Serradeil-Le Gal et al., "Nonpeptide vasopressin receptor antagonists: development of selective and orally active $V_{1a}$, $V_2$ and $V_{1b}$ receptor ligands," Progress in Brain Research, vol. 139, 2002, pp. 197-210.

Louise M. Burrell et al., "Vasopressin receptor antagonism—a therapeutic option in heart failure and hypertension," Experimental Physiology, Mar. 2000; 85 Spec; pp. 259S-265S.

Yoshitaka Yamamura et al., "OPC-41061, a Highly Potent Human Vasopressin $V_2$-Receptor Antagonist: Pharmacological profile and Aquaretic Effect by Single and Multiple Oral Dosing in Rats," The Journal of Pharmacology and Experimental Therapeutics, Dec. 1998, vol. 287, No. 3, pp. 860-867.

B. Mayinger et al., "Nonpeptide vasopressin antagonists: A new group of hormone blockers entering the scene, Experimental and Clinical Endocrinology & Diabetes," 1999, vol. 107; pp. 157-165.

Mareo Naitoh et al., "Effects of Chronic AVPV2R Blockade in Congestive Heart Failure in Sheep," Vasopressing and Oxytocin, Adv Exp Med Biol. 1998; 449, pp. 445-446.

Chagriya Kitiyakara et al., Vasopressin $V_2$-receptor antagonists: panaceas for hyponatremia?, Current Opinion in Nephrology and Hypertension, Sep. 1997, vol. 6, No. 5, pp. 461-467.

Ding-Li Xu et al., "Upregulation of Aquaporin-2 Water Channel Expression in Chronic Heart Failure Rat," The American Society for Clinical Investigation, Inc. Apr. 1997, vol. 99, No. 7, pp. 1500-1505.

J. G. Verbalis, "Vasopressin $V_2$ receptor antagonists," Journal of Molecular Endocrinology, 2002, vol. 29, pp. 1-9.

J. Donald Albright et al., "Recent Advances in the Discovery and Development of Vasopressin Antagonists: Peptide and Nonpeptide $V_{1a}$ and $V_2$ Receptor Antagonists," Current Pharmaceutical Design, vol. 3, pp. 615-632.

Junkankika 41, 150-154, 1997.

Gheorghiade Mihai et al., "Chronic effects of vasopressin receptor blockade with tolvaptan in congestive heart failure: A randomized double-blind trial," Circulation, vol. 102, No. 18Supplement, Oct. 31, 2000, pp. II.592.

Patent Abstracts of Japan, vol. 1999, No. 4, Apr. 30, 1999 & JP 11 021241 A, Otsuka Pharmaceuticals Co., Ltd., Jan. 26, 1999, Abstract.

Supplementary European Search Report, issued in EP 04 71 3672, Feb. 3, 2006.

Communication from European Patent Office issued in Application No. 04 713 672.6—2123, dated May 29, 2007, 6 pages.

Russia Office Action dated Dec. 13, 2007, Application No. 2005102110/14(002682).

V.A. Galkin, "Polyclinical therapy", Moscow, "Medicine", 2000, pp. 117-120.

V.G. Belikov, "Pharmaceutical chemistry", Moscow, "High school", 1993, vol. 1, pp. 43-47.

METHOD FOR TREATING SEVERE HEART FAILURE AND MEDICAMENT THEREFOR

CROSS REFERENCE TO RELATED APPLICATIONS

This application is a National Phase application based on PCT/JP2004/002085, filed on Feb. 23, 2004, the contents of which are incorporated herein by reference and claims the benefit of U.S. Provisional Application No. 60/448,878, filed on Feb. 24, 2003, the contents of which are incorporated herein by reference.

TECHNICAL FIELD

The present invention relates to a method for treating severe heart failure with a medicament comprising as an active ingredient a benzazepine compound, and a medicament useful therefor. More particularly, the present invention relates to a method for treating sever heart failure comprising administering to a patient in need thereof a therapeutically effective amount of a benzazepine compound of the formula (1):

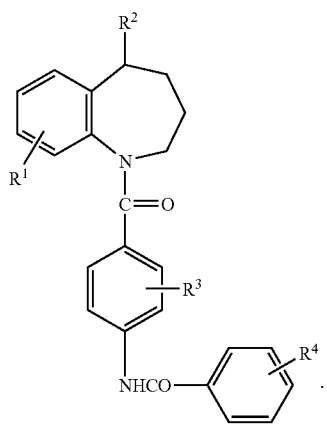

wherein $R^1$ is a hydrogen atom or a halogen atom, $R^2$ is a hydroxy group, or a group of the formula: —$NR^5R^6$ wherein $R^5$ and $R^6$ are the same or different and are each a hydrogen atom or a lower alkyl group, $R^3$ is a hydrogen atom, a halogen atom, a lower alkyl group, or a lower alkoxy group, $R^4$ is a halogen atom, a lower alkyl group or a lower alkoxy group, or a pharmaceutically acceptable salt thereof.

The present invention provides further a medicament for the treatment of the severe heat failure comprising as an active ingredient the above benzazepine compound (1) as well as use of the above benzazepine compound (1) for the preparation of a medicament useful for the treatment of severe heart failure.

BACKGROUND ART

It is known that the benzazepine compounds of the formula (1) have vasopressin antagonistic activity and are useful as a vasodilator, hypotensive agent, diuretic agent, platelet aggregation inhibitor, etc. (cf. WO 91/05549, U.S. Pat. Nos. 5,258, 510, 5,753,677, JP-A-6-80641) and further that those compounds are also useful as an oxytocin antagonist (WO 94/01113), a cataract treating agent (WO 94/18975, U.S. Pat. No. 5,827,862), a cerebral edema treating agent (JP-A-8-157368), a Meniere's disease treating agent (JP-A-10-120592), or an antiulcer agent (JP-A-7-188021).

Despite significant advances in the prevention and treatment of cardiovascular disease in the United States over the past two decades, as reflected by a 50% reduction in age-specific mortality from coronary artery disease (CAD) (American Heart Association, Heart and Stroke facts: 1996 statistical supplement, Page 15), the prevalence of heart failure has been steadily increasing (Massie B M, Shah N B, The heart failure epidemic, Curr. Opin. Cardiol. 1996, 11:221-226). This is most likely a result of the aging of the US population and the greater longevity of CAD patients. Approximately five million individuals currently have chronic congestive heart failure, and it has been estimated that 400,000 new cases of heart failure are diagnosed each year (Massie B M, Shah N B, The heart failure epidemic, Curr. Opin. Cardiol. 1996, 11:221-226). And approximately 20% of the patients need to be hospitalized each year for worsening of the disease state ("Cardium", published by Decision Resources (1998)). It has been shown that approximately 50% of patients with heart failure die within 5 years of their diagnosis (Konstam M, Dracut K, Baker D, et al., Heart failure: evaluation and care of patients with left ventricular dysfunction, AHCRP Publication No. 94-0612, Rockville (Md.): US Department of Health and Human Service; June 1994).

In the United States, the cost of treating heart failure has been estimated to be in excess of $12 billion annually and as high as $30 billion, excluding costs related to lost wages and productivity (Levitz K R, Lazenby H C, Cown C A, et al., National health expenditures, 1990, Health Care Fin Rev 1991, 13:29-54; O'Connell J B, Bristow M R, Economic impact of heart failure in the United States: time for a different approach, J Heart Lung Transplant 1994, 13:107-12). The cost of hospitalization alone exceeds $7 billion (O'Connell J B, Bristow M R, Economic impact of heart failure in the United States: time for a different approach, J Heart Lung Transplant 1994, 13:107-12).

Heart failure can be defined as a complex clinical syndrome characterized by abnormalities of left ventricular function and neurohormonal regulation, which in turn can result in effort intolerance, fluid retention, and reduced longevity.

The heart failure is classified to "acute heart failure" and "chronic heart failure" or "chronic heart failure in acute exacerbation" based on the clinical symptoms and the disease course.

The therapeutic measures for heart failure are entirely different depending on the conditions, i.e., whether it is in the chronic phase or in the acute phase. For the treatment of the chronic heart failure, it is treated so as to release the remaining heart failure symptom and to maintain in the stable state so that the symptom does not fall into chronic heart failure in acute exacerbation. On the other hand, when the patient falls into chronic heart failure in acute exacerbation, the symptom may possibly change rapidly for the worse and there is threat to life, and hence, from this viewpoint, it is necessary to take a life-saving measure by temporarily controlling the breath and blood pressure and administering a cardiotonic drug so as to moderate and stabilize the clinical symptoms, in hemodynamic viewpoint, by increasing cardiac output, decreasing intravascular circulation volume, and increasing renal blood flow.

Since most heart failures can not be treated by causal therapy, the symptoms change gradually for the worse with the lapse of time. Even though the cardiac function is temporarily recovered by a temporary symptomatic therapy, the function changes for the worse later and it is impossible to effect a permanent cure. The worsening rate varies depending on various conditions such as the kinds of underline diseases, severity of the disease, effectiveness of therapy, and living environment. Besides, the patients sometimes unexpectedly suddenly die, even while they have been in the favorable course of recovering. The patients of heart failure have bad prognosis as to the life. According to the statistics by Framingham Study in the U.S.A. including the data of all patients suffering from heart diseases, the 50% survival rate is shown in about 4 years since onset of the disease (Kannel, W B, et al., 1982, Mckee, P A, et al., 1982). Besides, in New York Heart Association Class, the patients suffering from the disease in the severity I of the disease, they show good prognosis, but the patients have the severity IV of the disease show the 50% survival rate in less than 1 year, that those having the severity II or III of the disease show the 50% survival rate in less than 4 years. Thus, the patients, who are diagnosed to be severe heart failure, have bad prognosis. (cf. Integrated Handbook of Internal Medicine, Volume 30, 1990, Nakayma Shoten).

DISCLOSURE OF INVENTION

The present inventors have intensively studied for seeking a method for the treatment of severe heart failure as well as a new medicament useful therefor. As the result, they have found that the benzazepine compounds of the formula (1) are effective for the treatment of severe heart failure, and have completed the present invention.

Thus, the present invention includes the following various embodiments.

[1] In a first embodiment, the present invention provides a new method for the treatment of severe heart failure, which comprises administering to a patient in need thereof a therapeutically effective amount of a benzazepine compound of the formula (1):

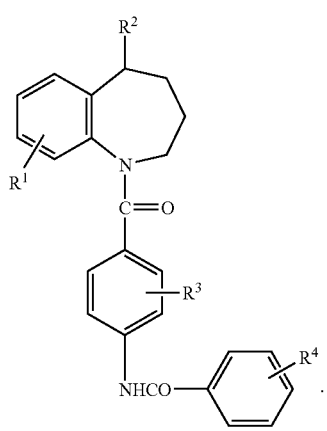

wherein $R^1$ is a hydrogen atom or a halogen atom, $R^2$ is a hydroxy group, or a group of the formula: —$NR^5R^6$ wherein $R^5$ and $R^6$ are the same or different and are each a hydrogen atom or a lower alkyl group, $R^3$ is a hydrogen atom, a halogen atom, a lower alkyl group, or a lower alkoxy group, $R^4$ is a halogen atom, a lower alkyl group or a lower alkoxy, or a pharmaceutically acceptable salt thereof.

[2] In another embodiment, the present invention provides a method for the treatment of severe heart failure according to the above [1], wherein the active compound (1) is administered in a dose of less than 0.6 mg/kg per day.

[3] In another embodiment, the present invention provides a method for the treatment of severe heart failure according to the above [1], wherein the active compound (1) is administered in a dose range from 0.1 mg/kg to less than 0.6 mg/kg per day.

[4] In another embodiment, the present invention provides a method for the treatment of severe heart failure according to the above [1], wherein the active compound (1) is administered in a dose of 15 mg to 45 mg/body per day.

[5] In another embodiment, the present invention provides a method for the treatment of severe heart failure according to the above [1], wherein the active compound (1) is 5-dimethylamino-1-[4-(2-methylbenzoylamino)benzoyl]-2,3,4,5-tetrahydro-1H-benzazepine.

[6] In another embodiment, the present invention provides a method for the treatment of severe heart failure according to the above [1], wherein the active compound (1) is 5-hydroxy-7-chloro-1-[2-methyl-4-(2-methylbenzoylamino)-benzoyl]-2,3,4,5-tetrahydro-1H-benzazepine.

[7] In another embodiment, the present invention provides a method for the treatment of severe heart failure according to the above [1], wherein the severe heart failure is acute heart failure or a chronic heart failure in acute exacerbation.

[8] In another embodiment, the present invention provides a method for the treatment of severe heart failure according to the above [1], wherein the severe heart failure is a severe heart failure of New York Heart Association Class: III and IV.

[9] In another embodiment, the present invention provides a new medicament for the treatment of severe heart failure which comprises as an active ingredient a benzazepine compound of the formula (1) or a pharmaceutically acceptable salt thereof.

[10] In another embodiment, the present invention provides a medicament according to the above [9], wherein the active compound (1) is 5-dimethylamino-1-[4-(2-methylbenzoylamino)benzoyl]-2,3,4,5-tetrahydro-1H-benzazepine.

[11] In another embodiment, the present invention provides a medicament according to the above [9], wherein the active compound (1) is 5-hydroxy-7-chloro-1-[2-methyl-4-(2-methylbenzoylamino)benzoyl]-2,3,4,5-tetrahydro-1H-benzazepine.

[12] In another embodiment, the present invention provides a pharmaceutical composition suitable for the treatment of severe heart failure which comprises as an active ingredient a benzazepine compound of the formula (1) or a pharmaceutically acceptable salt thereof in admixture with a conventional pharmaceutically acceptable carrier or diluent.

[13] In another embodiment, the present invention provides a pharmaceutical composition according to the above [12], wherein the active compound (1) is 5-dimethylamino-1-[4-(2-methylbenzoylamino)benzoyl]-2,3,4,5-tetrahydro-1H-benzazepine.

[14] In another embodiment, the present invention provides a pharmaceutical composition according to the above [12], wherein the active compound (1) is 5-hydroxy-7-chloro-1-[2-methyl-4-(2-methylbenzoylamino)benzoyl]-2,3,4,5-tetrahydro-1H-benzazepine.

[15] In another embodiment, the present invention provides a pharmaceutical composition according to any one of the above [12] to [14], wherein the active compound (1) is contained in an amount of 1 to 70% by weight based on the weight of the composition.

[16] In another embodiment, the present invention provides a use of a benzazepine compound of the formula (1) or a pharmaceutically acceptable salt thereof for manufacturing a medicament suitable for the treatment of severe heart failure.

[17] In another embodiment, the present invention provides a use of a benzazepine compound (1) or a pharmaceutically acceptable salt thereof according to the above [16], wherein the active compound (1) is 5-dimethylamino-1-[4-(2-methylbenzoylamino)benzoyl]-2,3,4,5-tetrahydro-1H-benzazepine.

[18] In another embodiment, the present invention provides a use of a benzazepine compound (1) or a pharmaceutically acceptable salt thereof according to the above [16], wherein the active compound (1) is 5-hydroxy-7-chloro-1-[2-methyl-4-(2-methylbenzoylamino)benzoyl]-2,3,4,5-tetrahydro-1H-benzazepine.

[19] In another embodiment, the present invention provides a use of a benzazepine compound (1) or a pharmaceutically acceptable salt thereof according to any one of the above [16] to [18], wherein the active compound (1) is contained in the medicament in a daily dosage unit of the range of less than 0.6 mg/kg.

BEST MODE FOR CARRYING OUT THE INVENTION

The medicament suitable for the method for treating severe heart failure of the present invention comprises as an active ingredient at least one of the benzazepine compounds of the above formula (1) or a pharmaceutically acceptable salt thereof.

In the description and claims, the groups in the above formula (1) denote the following groups.

The "halogen atom" denotes a fluorine atom, a chlorine atom, a bromine atom, or an iodine atom. The "lower alkyl group" denotes a straight chain or branched chain alkyl group having 1 to 6 carbon atoms, such as methyl, ethyl, propyl, isopropyl, butyl, tert-butyl, pentyl, or hexyl.

The "lower alkoxy group" denotes a straight chain or branched chain alkoxy group having 1 to 6 carbon atoms, such as methoxy, ethoxy, propoxy, isopropoxy, butoxy, tert-butoxy, pentyloxy, or hexyloxy.

Besides, the term "severe heart failure" in the description and claims means acute heart failure and chronic heart failure in acute exacerbation, for example, heart failures as classified in New York Heart Association Class: III and IV. New York Heart Association Class III and IV (The Criteria Committee of the New York Heart Association: Diseases of the Heart and Blood Vessels, Nomenclature and Criteria of Diagnosis, 6th ed. P. 110, Little, Brown & Co., Boston (1964)) are defined as follows: CLASS III. Patients with cardiac disease resulting in marked limitation of physical activity. They are comfortable at rest. Less than ordinary physical activity causes fatigue, palpitation, dyspnea, or anginal pain. CLASS IV. Patients with cardiac disease resulting in inability to carry on any physical activity without discomfort. Symptoms of cardiac insufficiency or of the anginal syndrome may be present even at rest. If any physical activity is undertaken, discomfort is increased.

According to the method of the present invention, the active benzazepine compound (1) is effective in an amount much less than the dose as previously claimed in the existing patent (WO 91/05549). That is, the compound (1) is used, for example, as an antiulcer drug, it is usually administered in a dose range from 0.6 to 50 mg/kg per day, e.g. 60 mg to 90 mg/body per day, but according to the studies by the present inventors, it has been found that when the compound (1) was administered in a dose range from 0.1 mg/kg to less than 0.6 mg/kg per day, and preferably in a dose of 15 mg to 45 mg/body per day, more preferably in a dose of about 30 mg/body per day, it was effective for decreasing of the body weight and increasing of the urine volume without undesirable side effects such as frequent urination, etc. and then can improve edema and mortality rate, and it has further been found that in the patients suffering from hyponatremia, it was observed increase of sodium level in serum.

Thus, according to the method of the present invention, even in the patients suffering from severe heart failure who have bad prognosis, the prognosis has been is significantly improved, and hence, the method of the present invention is useful for the treatment of severe heart failure.

The benzazepine compounds of the formula (1) and processes for preparing the same are disclosed in WO 91/05549, U.S. Pat. Nos. 5,258,510 and 5,753,677 as well as in the Japanese counterpart JP-A-6-80641.

The benzazepine compounds of the formula (1) can readily form a pharmaceutically acceptable acid addition salt with a pharmaceutically acceptable acid. The pharmaceutically acceptable acids include inorganic acids, such as sulfuric acid, hydrochloric acid, phosphoric acid, hydrobromic acid, etc. and organic acids such as acetic acid, p-toluenesulfonic acid, methanesulfonic acid, oxalic acid, maleic acid, fumaric acid, malic acid, tartaric acid, citric acid, succinic acid, benzoic acid, etc.

Among the benzazepine compounds of the formula (1), the compounds having an acidic group can readily form a salt with a pharmaceutically acceptable basic compound. The basic compounds include metal hydroxides such as sodium hydroxide, potassium hydroxide, lithium hydroxide, calcium hydroxide, etc.; alkali metal carbonates or hydrogen carbonates, such as potassium carbonate, sodium carbonate, sodium hydrogen carbonate, potassium hydrogen carbonate, etc.; and alkali metal alcoholates such as sodium methylate, potassium methylate, etc.

The active compounds (1) of the present invention are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations can be selected from various forms in accordance with the desired utilities, and the representative forms are tablets, pills, powders, solutions, suspensions, emulsions, granules, capsules, suppositories, injections (solutions, suspensions, etc.), and the like.

In order to form in tablets, there are used well known pharmaceutical carriers such as vehicles (e.g. lactose, white sugar, sodium chloride, glucose, urea, starch, xylitol, mannitol, erythritol, sorbitol, calcium carbonate, kaolin, crystalline cellulose, silicic acid, etc.), binders (e.g. water, ethanol, propanol, simple syrup, glucose solution, starch solution, gelatin solution, carboxylmethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the conventional carriers can be used and include, for example vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.) and the like. In the preparation of suppositories, the conventional carriers can be used and include, for example, polyethylene glycol, cacao butter, higher alcohol, higher alcohol esters, gelatin, semi-synthetic glycerides, and the like. Capsules can be prepared by charging a mixture of the compound of the present invention and the above carriers into hard gelatin capsules, soft capsules or hydroxypropylmethyl cellulose capsules (HPMC capsules) in usual manner. In the preparation of injections, the solutions, emulsions and suspensions are sterilized and are preferably made isotonic with the blood. In the preparation of these solutions, emulsions and suspensions, there are used conventional diluents such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with odium chloride, glucose, or glycerin in an amount sufficient to make them isotonic, and may also be incorporated with conventional solubilizer, buffers, anesthetizing agents. Moreover, the pharmaceutical preparations may optionally be incorporated with coloring agents, preservatives, perfumes, flavors, sweetening agents, and other medicaments, if required.

The amount of the active compound (1) to be incorporated into the pharmaceutical composition of the present invention is not specified but may be selected from a broad range, but usually, it is preferably in the range of 1 to 70% by weight, more preferably 5 to 50% by weight, based on the weight of the composition.

The suitable method for administration of the medicament of the present invention may be determined in accordance with various forms of preparations, ages, sexes and other conditions of the patients, the degree of severity of diseases, and the like. For example, tablets, pills, solutions, suspensions, emulsions, granules and capsules are administered orally. The injections are intravenously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the active compound of the present invention may be selected in accordance with the usage, ages, sexes and other conditions of the patients, the degree of severity of the diseases, and the like, but it is usually in the range of less that 0.6 mg/kg per day, preferably from 0.1 mg/kg to less than 0.6 mg/kg per day. The suitable dose is in the range of 15 mg to 45 mg/body per day.

EXAMPLES

The present invention is illustrated in more detail by the following preparations and experiments, but should not be construed to be limited thereto.

Preparation 1

| | |
|---|---|
| 5-Dimethylamino-1-[4-(2-methylbenzoylamino)-benzoyl]-2,3,4,5-tetrahydro-1H-benzazepine | 150 g |

-continued

| | |
|---|---|
| Avicel (trade name, manufactured by Asahi Chemical Industry, Co., Ltd., Japan) | 40 g |
| Corn Starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active compound of the present invention, Avicel, corn starch and magnesium stearate are mixed and kneaded and the mixture is tabletted by using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

| | |
|---|---|
| 5-Hydroxy-7-chloro-[2-methyl-4-(2-methylbenzoylamino)-benzoyl]-2,3,4,5-tetrahydro-1H-benzazepine | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium laurylsulfate | 3.0 g |
| Dry magnesium stearate | 3.0 g |
| Ethanol | q.s. |

The active compound of the present invention, citric acid, lactose, dicalcium phosphate, Pullonic F-68 and sodium laurylsulfate are mixed.

The mixture is screened with No. 60 screen and is granulated with an alcohol solution containing polyvinylpyrrolidone, Carbowax 1500 and Carbowax 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are varnished and dusted with talc, in order to guard them from wetting. Undercoating is applied to the core tablets. In order to administer the tablets orally, the core tablets are varnished several times. In order to give round shape and smooth surface to the tablets, further undercoating and coating with a lubricant are applied thereto. The tablets are further coated with a coloring coating material until the desired colored tablets are obtained. After drying, the coated tablets are polished to obtain the desired tablets having uniform gloss.

Preparation 3

| | |
|---|---|
| 5-Hydroxy-7-chloro-[2-methyl-4-(2-methylbenzoylamino)-benzoyl]-2,3,4,5-tetrahydro-1H-benzazepine | 5 g |

-continued

| | |
|---|---|
| Polyethylene glycol (molecular weight; 4000) | 0.3 g |
| Sodium chloride | 0.9 g |
| Polyoxyethylene sorbitan monooleate | 0.4 g |
| sodium metabisulfite | 0.1 g |
| Methyl paraben | 0.18 g |
| Propyl paraben | 0.02 g |
| Distilled water for injection | 10.0 ml |

The above parabens, sodium metabisulfite and sodium chloride are dissolved in distilled water of about half volume of the above with stirring at 80° C. The solution thus obtained is cooled to 40° C., and the active compound of the present invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

Experiments (1) Methods:

To patients of severe heart failure (i.e., patient in acute heart failure or chronic heart failure in acute exacerbation, New York Heart Association Class III and IV) was administered 5-hydroxy-7-chloro-1-[2-methyl-4-(2-methylbenzoylamino)benzoyl]-2,3,4,5-tetrahydro-1H-benzazepine at a dose of 30, 60 or 90 mg/day for a period of 60 days, which period began from the duration of hospitalization to after being discharged from hospital (details thereof are shown in Table 1).

(2) Results:

The results are shown in Tables 2 to 7.

As to the statistical analysis, the data in Table 2 was analyzed by ANOVA method, and the data in Tables 3 and 4 were analyzed by ANCOVA method, and the data in Table 5 was analyzed by Log-Rank test.

When the dosages in this experiment were converted to a daily dose per 1 kg of body weight, they were $0.371\pm0.096$ mg/kg (n=77) in the 30 mg-treated group, $0.769\pm0.205$ mg/kg (n=83) in the 60 mg-treated group, and $1.149\pm0.283$ mg/kg (n=76) in the 90 mg-treated group (all in mean$\pm$SD).

As is shown in the results, in the 30 mg-treated group, the total urine output was increased (Table 2), and the body weight was decreased (Table 3). In addition, patients of hyponatremia at baseline (patients having the serum sodium concentration lower than the normal (less than 136 mEq/L)) showed the increase of serum sodium concentration (Table 4).

In the same experiment, the mortality rate throughout the entire period from the period of hospitalization until the termination of medication at the outpatient department was significantly lower in the 30 mg-treated group than the control group, which was analyzed with taking into consideration of the time in days from the beginning of the medication until the death event (Log-Rank test) (Table 5).

In addition, in the group treated with the lowest dose of 30 mg, the urinary frequency event rate as an adverse experience was lower (Table 6), and the discontinued rate due to adverse experiences was lower (Table 7), as compared with the data of the groups treated with higher doses. As a result, it is apparent that the compound of the present invention exhibits excellent therapeutic effects on severe heart failure by controlling a dose thereof less than 0.6 mg per 1 kg of body weight per day.

TABLE 1

Study synopsis

Name of Product:
5-Hydroxy-7-chloro-[2-methyl-4-(2-methylbenzoyl-amino) benzoyl]-2,3,4,5-tetrahydro-1H-benzazepine
(A)

| | |
|---|---|
| Study Title: | Multicenter, Randomized, Double-Blind, Placebo-Controlled, Study of (A) to Evaluate the Effects of (A) on the Acute and Chronic Outcomes of Patients with Worsening Congestive Heart Failure |
| Clinical Phase: | IIB |
| Treatment Indication: | Patients with Worsening Congestive Heart Failure |
| Objective(s): | To assess the efficacy of three doses of (A) or placebo in conjunction with optimal current therapy (as determined by the Investigator) with up to 10 days of acute inpatient study drug dosing, followed by 7 weeks of outpatient dosing. |
| Study Design: | Multicenter, randomized, double-blind, placebo-controlled, parallel groups The study consisted of a Screening Day, up to a 10-day inpatient period followed by a 7-week outpatient period. Patients returned for outpatient assessments on Outpatient Weeks 1, 3, 5, and 7. A follow-up telephone contact occurred 7 days after the last dose of study drug. Four groups of about 80 patients were randomized to receive once daily for up to 59 days: 1) placebo, 2) 30 mg of (A), 3) 60 mg of (A), or 4) 90 mg of (A) All patients continued to receive conventional therapy which may include diuretics, digoxin, ACE inhibitors, hydralazine, nitrates, beta blockers |

TABLE 1-continued

Study synopsis

| | |
|---|---|
| Subject Population: | Patients hospitalized for worsening heart failure<br>NYHA class III-IV<br>Male and Female<br>≧18 years of age |
| Test Product, Dose, Mode of Administration: | (A) 30 mg, 60 mg, 90 mg, or placebo oral tablets |

| | |
|---|---|
| Endpoints: | Efficacy: |
| INPATIENT PRIMARY: | Body weight changes at 24 hours post dosing |
| INPATIENT SECONDARY: | NYHA classification, dyspnea, orthopnea, body weight at discharge, edema, jugular venous distention, rales, hepatomegaly, urine output, daily serum electrolytes, length of stay, diuretic usage, patient and physician assessed symptom score |
| OUTPATIENT PRIMARY: | Worsening of heart failure defined as any of the following: 1. Hospitalization, 2. Unscheduled visit for CHF to an emergency department, outpatient clinic, or observations unit associated with need for either increased therapy or new therapy for heart failure, 3. Death. Rates of withdrawal due to worsening heart failure, and time to withdrawal was analyzed. |
| OUTPATIENT SECONDARY: | NYHA classification, edema, body weight, jugular venous distention, rales, hepatomegaly, dyspnea, orthopnea, urine output, serum electrolytes, patient and physician assessed symptom score |
| SAFETY: | Adverse events, vital signs, clinical laboratory tests, PT/APTT, 12-lead electrocardiograms, and physical examinations |
| PK: | Plasma (A) and metabolite concentrations |

TABLE 2

Total urine output on Day 1 in patients treated with (A)

| Day | Placebo | 30 mg | 60 mg | 90 mg |
|---|---|---|---|---|
| 1 | 2296.46 ± 1134.13 (76) | 4056.16 ± 2310.23** (73) | 4175.15 ± 2695.44** (82) | 4127.27 ± 2050.81** (73) |
| 2 | 2317.20 ± 1168.09 (61) | 3905.61 ± 1942.03** (67) | 3699.26 ± 2094.02** (74) | 3961.73 ± 2129.11** (64) |
| 3 | 1164.27 ± 1003.99 (4B) | 3579.04 ± 1867.86** (52) | 3420.41 ± 1902.77** (54) | 4069.32 ± 2306.07** (50) |
| 6 | 1896.36 ± 1054.42 (22) | 3146.67 ± 1618.09 (33) | 3684.56 ± 2472.45* (32) | 4188.23 ± 2275.15** (30) |
| 7 | 1941.67 ± 1349.94 (12) | 2662.81 ± 1507.51 (16) | 4230.00 ± 1691.43* (17) | 3915.12 ± 2101.53 (17) |
| 9 | 1989.17 ± 386.14 (6) | 2908.00 ± 475.59 (5) | 3753.18 ± 2415.48 (11) | 2421.43 ± 1391.12 (7) |

Mean ± SD
The number in parentheses indicates the number of patients measured.
**p < 0.01,
*p < 0.05, Significant difference vs. placebo

TABLE 3

Mean change in body weight from baseline in patients treated with (A)

| Time | Placebo | 30 mg | 60 mg | 90 mg |
|---|---|---|---|---|
| Day 1 | −0.87 ± 1.95 (78) | −2.14 ± 2.63** (76) | −2.10 ± 1.80** (76) | −1.90 ± 2.87** (74) |
| Day 2 | −1.45 ± 2.52 (57) | −3.49 ± 3.80** (63) | −3.03 ± 2.48 (65) | −2.84 ± 3.16** (61) |
| Day 3 | −2.46 ± 2.42 (45) | −4.78 ± 4.14** (49) | −3.93 ± 3.33* (47) | −2.65 ± 4.22 (45) |
| Discharge | −2.56 ± 3.17 (78) | −4.37 ± 4.69** (76) | −4.60 ± 4.67** (82) | −3.75 ± 4.18 (76) |
| Week 1 | −1.80 ± 4.53 (63) | −2.71 ± 4.93 (65) | −2.73 ± 5.45 (59) | −3.23 ± 4.46 (53) |
| Week 7 | −1.24 ± 5.16 (59) | −2.12 ± 5.16 (54) | −2.87 ± 6.67 (54) | −2.23 ± 5.19 (53) |
| Last Visit | −1.32 ± 4.77 (78) | −2.42 ± 5.37 (76) | −3.60 ± 6.38 (82) | −2.39 ± 5.20 (76) |

Mean ± SD
The number in parentheses indicates the number of patients measured.
**p < 0.01,
*p < 0.05, Significant difference vs. placebo

TABLE 4

Serum sodium concentration in patients treated with (A)

| Time | Placebo | 30 mg | 60 mg | 90 mg |
|---|---|---|---|---|
| Baseline | 132.81 ± 2.37 (16) | 132.13 ± 3.44 (15) | 130.86 ± 4.00 (22) | 133.07 ± 2.52 (15) |
| Day 1 | 134.75 ± 4.34 (16) | 136.00 ± 3.96 (15) | 135.77 ± 6.16 (22) | 137.13 ± 4.82 (15) |
| Day 2 | 135.45 ± 5.03 (11) | 135.09 ± 5.07 (11) | 137.29 ± 3.02 (17) | 137.00 ± 4.60 (15) |
| Day 3 | 134.78 ± 4.76 (9) | 135.13 ± 5.38 (8) | 138.62 ± 4.44 (13) | 136.45 ± 4.59 (11) |
| Discharge | 133.56 ± 3.10 (16) | 136.13 ± 4.61 (15) | 137.18 ± 4.56* (22) | 137.13 ± 3.02 (15) |
| Week 1 | 133.77 ± 4.75 (13) | 138.25 ± 4.22* (12) | 136.88 ± 5.82* (16) | 136.13 ± 3.64 (8) |
| Week 7 | 134.67 ± 5.52 (9) | 137.60 ± 4.65 (10) | 139.36 ± 4.76* (11) | 138.00 ± 5.73 (6) |
| Last Visit | 133.88 ± 5.15 (16) | 137.00 ± 5.04 (15) | 136.18 ± 5.94 (22) | 136.60 ± 5.17 (15) |

Mean ± SD
The number in parentheses indicates the number of patients measured.
**p < 0.01,
*p < 0.05, Significant difference vs. placebo

TABLE 5

Mortality of the patients treated with (A)

| Events | Placebo (80) | 30 mg (78) | 60 mg (84) | 90 mg (77) |
|---|---|---|---|---|
| Number off Death | 7 | 3 | 8 | 2 |
| Event Rate (%) | 8.7% | 3.8% | 9.5% | 2.5% |
| P-value | | 0.0326 | 0.7862 | 0.1460 |

The number in parentheses indicated the number of patients randomized in the group.
Analysis on "Time to Death (on therapy)" were performed by Log-Rank test.

TABLE 6

Adverse events observed in patients treated with (A)

| Adverse Event | Placebo (79) | 30 mg (78) | 60 mg (84) | 90 mg (76) |
|---|---|---|---|---|
| Urinary Frequency | 1 | 1 | 3 | 4 |
| Event Rate (%) | 1.3% | 1.3% | 3.6% | 5.3% |

The number in parentheses indicated the number of patients randomized in the group.

TABLE 7

Discontinued cases due to adverse experiences in patients treated with (A)

| Reason of Discontinuation | Placebo (80) | 30 mg (78) | 60 mg (84) | 90 mg (77) |
|---|---|---|---|---|
| Adverse Experience | 12 | 14 | 25 | 17 |
| Event Rate (%) | 15.0% | 17.9% | 29.8% | 22.1% |

The number in parentheses indicated the number of patients randomized in the group.

INDUSTRIAL APPLICABILITY

The method for the treatment of severe heart failure of the present invention is quite useful in the treatment of severe heart failure, i.e. acute heart failure and chronic heart failure in acute excerbation. In addition, the method of the present invention is excellently safe with few side effects. Thus, the present invention provides a method for the treatment of severe heart failure by administering to a patient a benzazepine compound (1) or a pharmaceutically acceptable salt thereof, and a pharmaceutical composition containing said benzazepine compound (1) or a pharmaceutically acceptable salt thereof as well as a use of said active compound for manufacturing a medicament suitable for the treatment of severe heart failure.

The invention claimed is:

1. A method for treating severe heart failure of New York Heart Association Class IV, comprising administering to a patient in need thereof a therapeutically effective amount of an active compound, 5-hydroxy-7-chloro-1-[2-methyl-4-(2-methyl benzoylamino)benzoyl]-2,3,4,5-tetrahydro-1H-benzazepine or a pharmaceutically acceptable salt thereof in a daily dose of less than 0.6 mg/kg.

2. The method according to claim 1, wherein the daily dose is in the range from 0.1 mg/kg to less than 0.6 mg/kg.

3. A method for treating severe heart failure of New York Heart Association Class IV, comprising administering to a patient in need thereof a therapeutically effective amount of an active compound, 5-hydroxy-7-chloro-1-[2-methyl-4-(2-methylbenzoylamino)benzoyl]-2,3,4,5-tetrahydro-1H-benzazepine or a pharmaceutically acceptable salt thereof in a daily dose of 15 to 45 mg.

4. The method according to claim 3, comprising administering to the patient the active compound in a daily dosage of 30 mg.

* * * * *